(12) United States Patent
Murphy

(10) Patent No.: US 6,749,595 B1
(45) Date of Patent: Jun. 15, 2004

(54) CEMENT DELIVERY NEEDLE

(76) Inventor: Kieran P. J. Murphy, 119 Beechdale Rd., Baltimore, MD (US) 21210

( * ) Notice: Subject to any disclaimer, the term of this patent is extended or adjusted under 35 U.S.C. 154(b) by 312 days.

(21) Appl. No.: 09/594,167

(22) Filed: Jun. 15, 2000

(51) Int. Cl.[7] .............................................. A61M 31/00
(52) U.S. Cl. ...................... 604/500; 604/506; 606/185
(58) Field of Search .................................. 606/184, 185; 604/164.01, 164.04, 164.07, 164.09, 264, 500, 506

(56) References Cited

U.S. PATENT DOCUMENTS

| | | | | |
|---|---|---|---|---|
| 2,919,692 | A | * | 1/1960 | Ackerman .................. 606/184 |
| 3,628,524 | A | * | 12/1971 | Jamshidi ..................... 606/184 |
| 4,013,080 | A | | 3/1977 | Froning |
| 4,356,828 | A | * | 11/1982 | Jamshidi |
| 4,518,383 | A | | 5/1985 | Evans |
| 4,838,282 | A | * | 6/1989 | Strasser et al. ............. 606/184 |
| 4,958,901 | A | | 9/1990 | Coombs |
| 4,969,888 | A | | 11/1990 | Scholten et al. |
| 5,108,404 | A | | 4/1992 | Scholten et al. |
| 5,242,448 | A | | 9/1993 | Pettine et al. |
| 5,628,734 | A | | 5/1997 | Hatfalvi |
| 6,019,776 | A | * | 2/2000 | Preissman et al. |
| 6,048,336 | A | | 4/2000 | Gabriel |
| 6,050,977 | A | | 4/2000 | Adams |
| 6,074,373 | A | | 6/2000 | Sudo et al. |
| 6,221,029 | B1 | * | 4/2001 | Mathis et al. |
| 6,248,110 | B1 | * | 6/2001 | Reiley et al. |

FOREIGN PATENT DOCUMENTS

| | | |
|---|---|---|
| WO | 9918865 | 4/1999 |
| WO | 9918866 | 4/1999 |
| WO | 9949819 | 10/1999 |

* cited by examiner

*Primary Examiner*—Mark Bockelman
(74) *Attorney, Agent, or Firm*—Richard J. Godlewski

(57) ABSTRACT

A cement delivery needle for use in performing vertebroplasty is provided. In one embodiment, there is provided a cement delivery needle with a sheath and an insert. The sheath has an inlet to receive a bone cement and a tapered outlet for expressing the cement into a vertebral body. The insert is receivably removable within the sheath. The insert also has a tip that is alignable with the outlet, when the insert is inserted into the sheath, to present a continuous edge. When the edge is inserted into a resistant material, an application of force to the needle creates an opening in the material to allow the needle to pass therethrough.

6 Claims, 12 Drawing Sheets

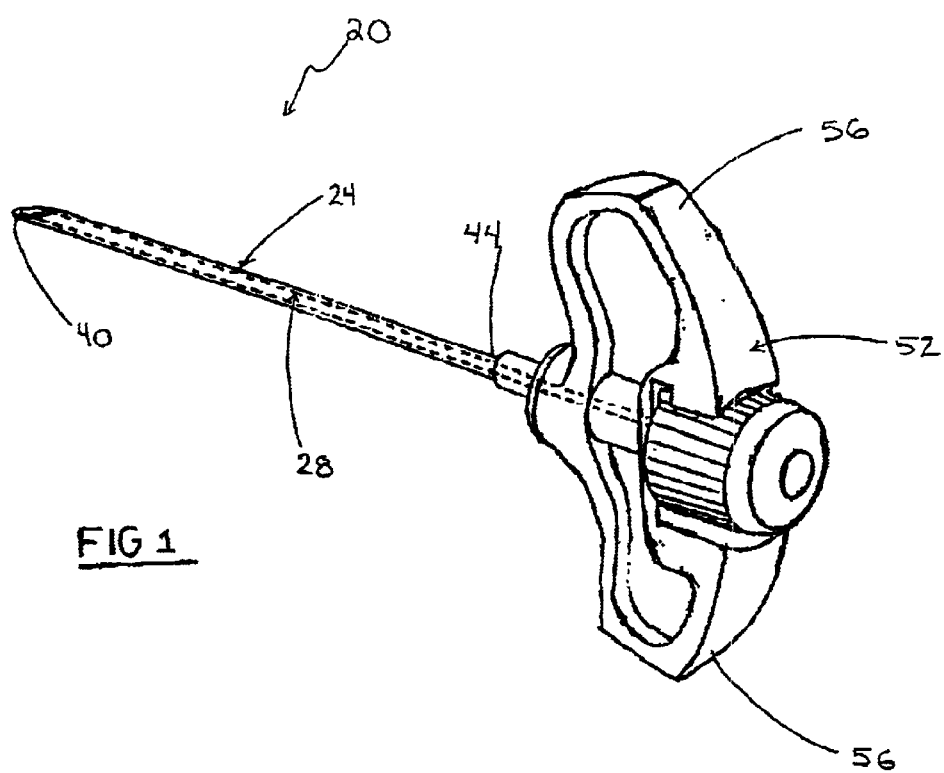

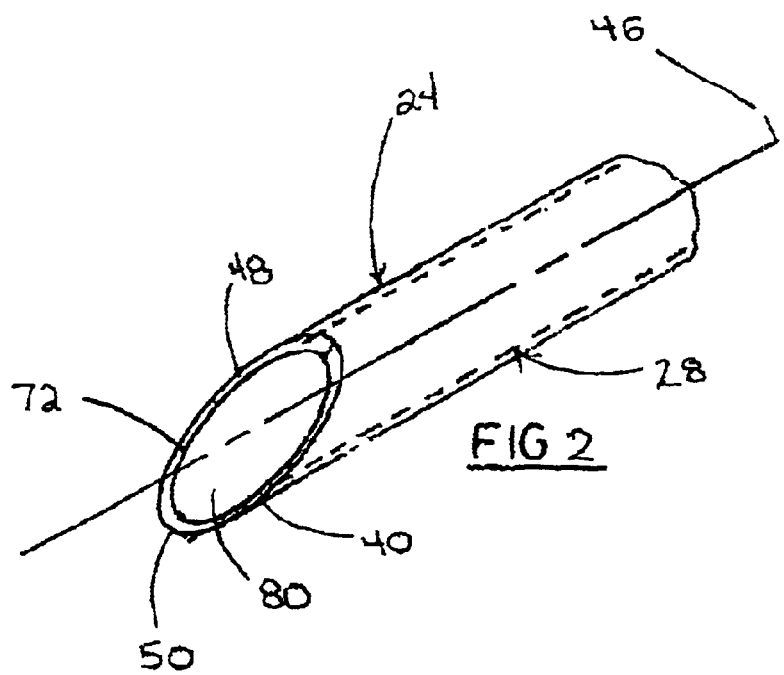
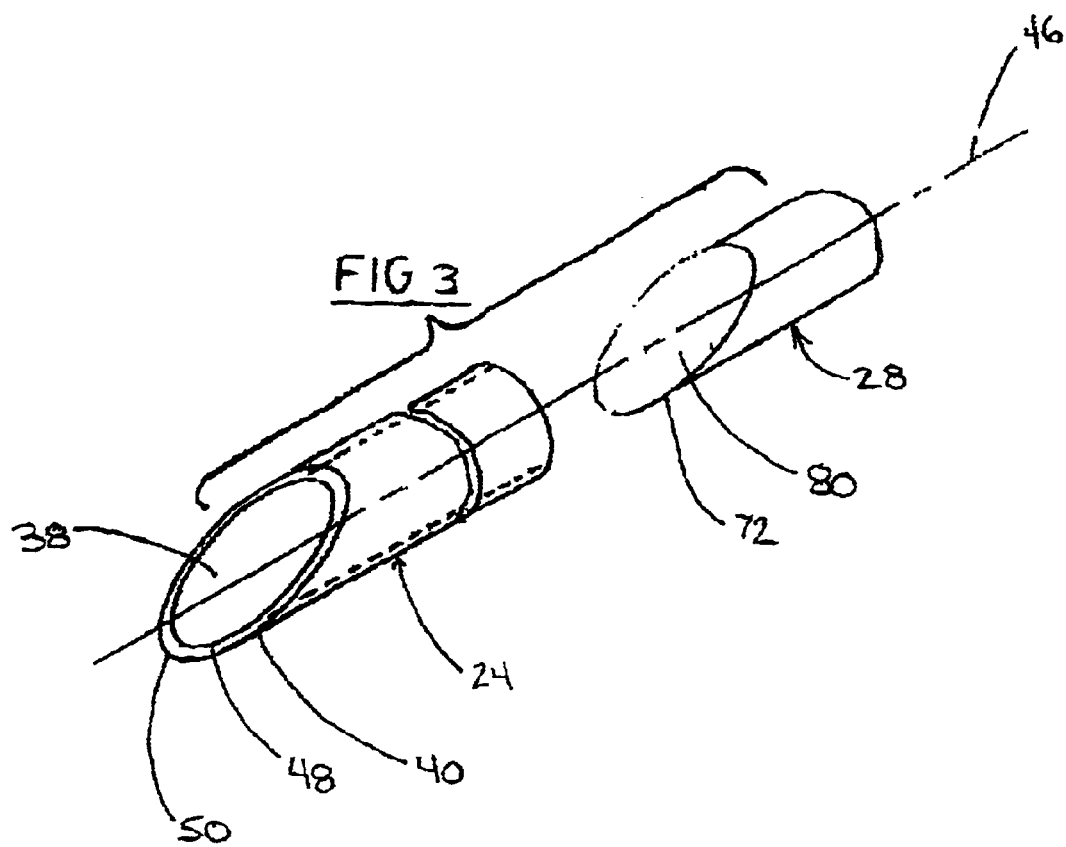

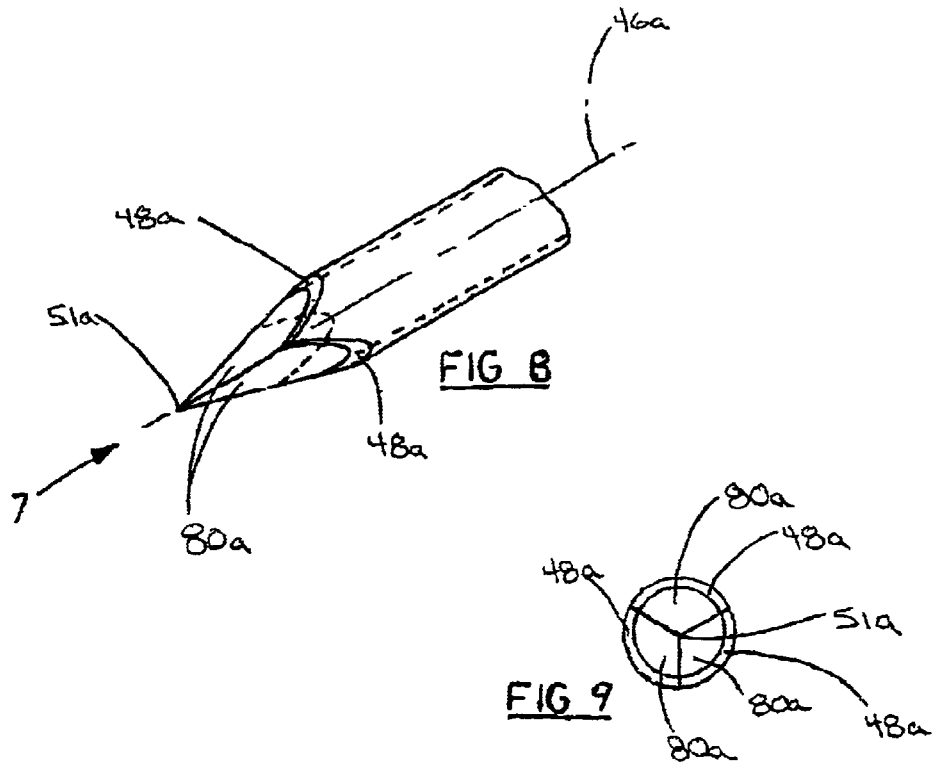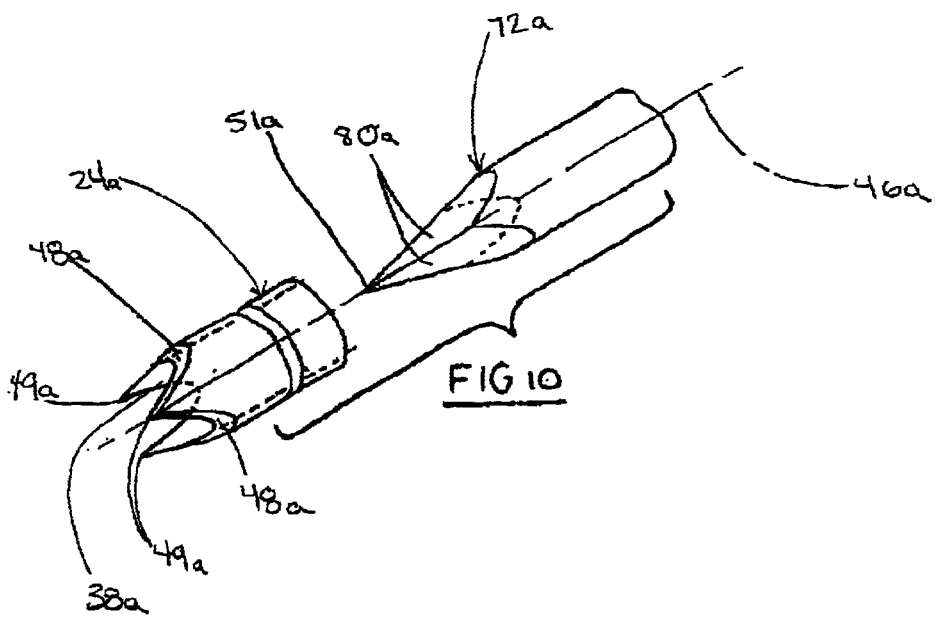

CEMENT DELIVERY NEEDLE

BACKGROUND OF THE INVENTION

1. Field of the Invention

In one of its aspects, the present invention relates to a surgical needle, more particularly to a needle for expressing bone cement into a vertebral body. In another of its aspects, the present invention relates to a method for passing a needle into a vertebral body.

2. Description of the Prior Art

Percutaneous vertebroplasty involves the injection of a bone cement or suitable biomaterial into a vertebral body via percutaneous route under X-ray guidance. The cement is injected as a semi-liquid substance through a needle that has been passed into the vertebral body, generally along a transpedicular or posterolateral approach. The three main indications are benign osteoporotic fractures, malignant metastatic disease and benign tumours of the bone.

Percutaneous vertebroplasty is intended to provide structural reinforcement of a vertebral body through injection, by a minimally invasive percutaneous approach, of bone cement into the vertebral body. See, for example, Cotton A., et al "Percutaneous vertebroplasty: State of the Art." *Radiograhics March–April;* 1998, 18(2):311–20; discussion at 320-3. Percutaneous vertebroplasty can result in increased structural integrity, decreased micromotion at the fracture site, and possibly a destruction of pain fibres due to the heat of the bone cement as it polymerizes and sets. Complete pain relief can be achieved in up to eighty percent of patients. As known to those of skill in the art, the cement should have properties that, when injected, can increase vertebral body stiffness and compressive strength. It is generally preferred that the cement is liquid enough to flow into fracture planes and to fuse them. There is some debate about the appropriate thermal properties, but it is believed by some that the heating effect can be beneficial and cause death to local nerve endings involved in pain stimulation. It is generally accepted that most pain relief is achieved due to increased structural integrity.

Generally, when performing vertebroplasty, a needle of an appropriate gauge (such as eleven gauge or thirteen gauge in a smaller vertebral body) is passed down the pedicle until it enters the vertebral body and reaches the junction of the anterior and middle thirds. Great skill is usually required to insert the needle at a suitable angle and pass the needle through the periosteum, down the pedicle and into the vertebral body. Also, insertion of the needle generally requires a large applied force. Specifically, a large force can be required when entering the cortex and in the transition from the pedicle to the vertebral body.

A suitable cement is prepared, injected through the needle and into the vertebral body, under lateral X-ray projection fluoroscopy imaging. The injection is stopped as the cement starts to extend into some unwanted location such as the disc space or towards the posterior quarter of the vertebral body, where the risk of epidural venous filling and hence spinal cord compression is greatest. The injection is also discontinued if adequate vertebral filling is achieved.

In many needles of the prior art, there is a step or change in the angle of the taper at the needle tip. This change in the taper can cause an increase in the required applied force when inserting the needle. The additional applied force can result in a rib fracture. Thus, needles of the prior art can be difficult to insert into the patient. Presently, it is common for a hammer to be used to overcome the force required to insert the needle into the vertebral body.

During insertion of the needle, operator control is reduced due to the greater required applied force. Further, needles are difficult to accurately insert because of the large required applied force.

Prior art needles used in vertebroplasty have certain limitations. Needles such as the MDTECH, bone marrow biopsy/aspiration needle, ref DBMNJ1104T, from Medical Device Technologies, Inc, 3600 S.W. $47^{th}$ Avenue, Gainsville, Fla. 32608, have been used for the delivery of bone cement. These needles are designed for obtaining biopsy samples and not for injection of cement. The end of the needles are tapered which can reduce the volume of bone cement injected. On average, about 4 to 5 $cm^3$ of cement can be injected per side. Further, the tip of the needles have a step or a change in the angle of taper, as discussed above, thus making them difficult to insert as resistance is encountered both at the tip and at the step. A large force is required first for the tip to pierce the periosteum and the cortex, and second, a greater force is required for the step of the needle to pass through the periosteum and cortex. Again, additional force is required for the needle tip to pass through the transition from the pedicle to the vertebral body and an even greater force is required for the step of the needle to pass through this transition.

There are many other biopsy needles that can be used for the injection of cement, however these needles suffer from certain limitations. Many needles are used for retrieving soft-tissue biopsy samples and are not suitable for piercing hard tissue such as bone. Also, many needles do not have an end suitable for attachment of a syringe. Further, these needles may not have a handle suitable for applying sufficient force to pierce the cortex or to pass the transition from the pedicle to the vertebral body. Also, many biopsy needles have an end with an internal taper that can reduce the volume of cement that can be injected.

Other needles for use in vertebroplasty are disclosed in International publications numbers WO 99/18865 and WO 99/18866. These instruments include a self-tapping, threaded stylet end for tapping into hard tissue. A cannula fits over the stylet and the threaded end is used to draw the cannula into the desired position. A syringe can be attached to the cannula for injection of the cement. The stylet of this needle is rotatably screwed into the desired position. When the stylet is in the desired position, the cannula is rotatably screwed into position. Alternatively, the stylet can be pushed into the desired position or can be positioned by a ratchet assembly and action.

During insertion of these needles, more control can be gained by the slow rotation of the stylet into place, followed by the cannula being moved into place. Therefore, greater time is required to insert this needle than those needles of the prior art. Also, the needle construction is somewhat complex. The screw portion of the stylet can break off in hard bone or can slide on hard bone.

Thus, there exists a need in the art for cement delivery needle which can withstand the rigours of insertion in a patient dur percutaneous vertebroplasty. It would be desirable if such a needle could be readily constructed and readily put into use by those of skill in the art.

SUMMARY OF THE INVENTION

It is an object of the present invention to provide a novel cement delivery needle which obviates or mitigates at least one of the above-mentioned disadvantages of the prior art.

It is another object of the present invention to provide a novel method for passing a needle into a vertebral body.

In one aspect of the present invention, there is provided a cement delivery needle, for use in performing vertebroplasty, having a sheath and an insert. The sheath has an inlet to receive a bone cement and a tapered outlet for expressing the cement into a vertebral body. The insert is receivably removable within the sheath. The insert also has a tip that is alignable with the outlet, when the insert is inserted into the sheath, to present a continuous edge.

In another aspect of the present invention, there is provided a method for performing vertebroplasty on a vertebral body. A cement delivery needle is inserted into a patient, the cement delivery needle having a sheath with an inlet to receive a bone cement and a tapered outlet for expressing the cement into the vertebral body. An insert is receivably removable within the sheath. The insert has a tip that is alignable with the outlet when the insert is received by the sheath to present a continuous edge. When the edge is inserted into a resistant material, an application of force to the needle creates an opening in the material to allow the needle to pass therethrough. The needle is passed down a pedicle and into the vertebral body. The insert is slideably removed from the sheath while maintaining the sheath in the vertebral body. A suitable injector is connected to the sheath. The bone cement is injected through the sheath and into the vertebral body.

In still another aspect of the present invention, there is provided a method for passing a needle into a vertebral body. The needle has a sheath with an inlet and a tapered outlet. The needle also has an insert that is receivably removable within the sheath. The insert has a tip that can be inserted into the sheath and aligned with the outlet to present a continuous edge. The method comprises the steps of piercing the skin lying above the periosteum of a vertebrae along a transpedicular approach. Next, a first force is applied along the needle to cause the edge to pierce the periosteum and cortex and create an opening large enough for the needle to pass therethrough. The needle is then passed through a pedicle. A second force is applied to the needle to cause the edge to pierce a junction of the pedicle and the vertebral body to create an opening of sufficient size to allow the needle to pass therethrough. The needle is then passed into the vertebral body.

BRIEF DESCRIPTION OF THE DRAWINGS

Embodiments of the present invention will be described with reference to the accompanying drawings, in which:

FIG. 1 illustrates a perspective view of one embodiment of the present cement delivery needle;

FIG. 2 illustrates a partial perspective view of the needle in FIG. 1;

FIG. 3 illustrates an exploded partial perspective view of the needle in FIG. 1;

FIG. 8 illustrates a partial perspective view of the cement delivery needle in FIG. 7;

FIG. 9 illustrates a partial end view of the cement delivery needle in FIG. 7;

FIG. 10 illustrates an exploded partial perspective view of the needle in FIG. 7;

DETAILED DESCRIPTION OF THE PREFERRED EMBODIMENTS

Figure 4:
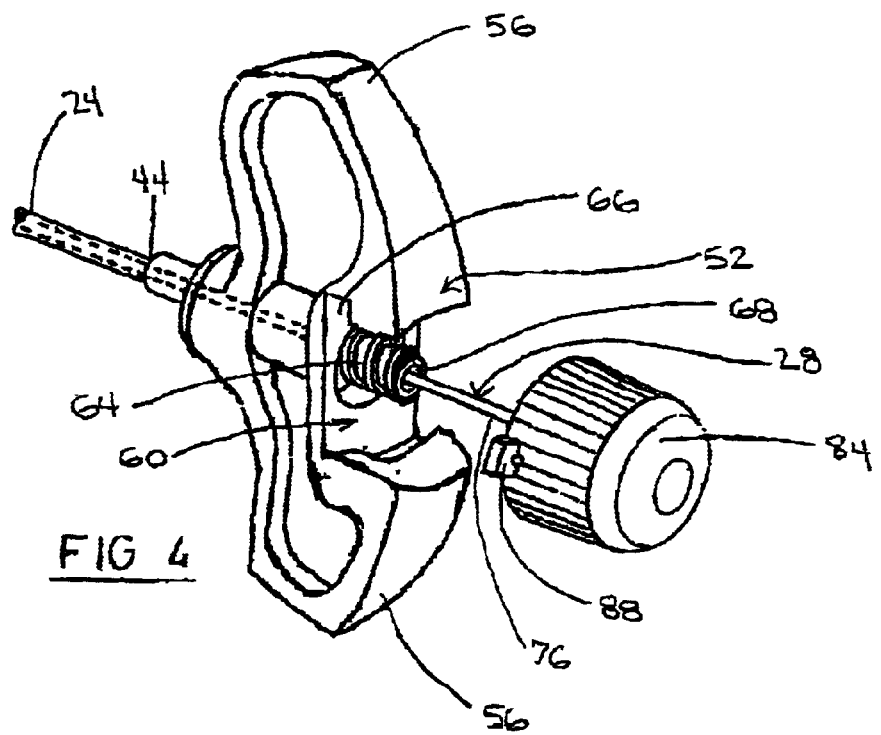
FIG. 4 illustrates a partial perspective view of the needle in FIG. 1 with the insert partly removed from the sheath.

With reference to FIGS. 1–3, a cement delivery needle according to an embodiment of the present invention is indicated generally at 20. Needle 20 is preferably used for expressing bone cement or a suitable biomaterial into a vertebral body. In a present embodiment, needle 20 is constructed of surgical grade stainless steel but other suitable materials that are also compatible with magnetic resonance imaging can be used, as will occur to those of skill in the art. Cement delivery needle 20 generally consists of a sheath 24 and an insert 28 receivably removable within the sheath. As shown in FIGS. 13–17, insert 28 is receivable within sheath 24 for insertion of needle 20 into a vertebral body 32 via percutaneous route. Insert 28 is removable from sheath 24 to facilitate the injection of a cement 36 into vertebral body 32.

Referring to FIGS. 1–3, sheath 24 is generally a hollow cylinder with an interior 38, an outlet 40 and an inlet 44. Sheath 24 is cylindrically centred about an axis 46. Axis 46 is shown as a dashed line in FIGS. 1–3. In a present embodiment, the cross-sectional area of interior 38 is not reduced at outlet 40. Thus, the diameter of interior 38, is substantially constant from inlet 44 to outlet 40. Outlet 40 is bevelled such that it presents a single planar ace 48. It is believed that planar face 48 can be at an angle of from about 15° to about 75° to axis 46. Planar face 48 can also be at an angle of from about 30° to about 60° to axis 46. It will be understood by those of skill in the art, however, that planar face 48 can be at any suitable, desired angle. In the present embodiment, planar face 48 of sheath 24 defines a leading edge 50.

Figure 5:
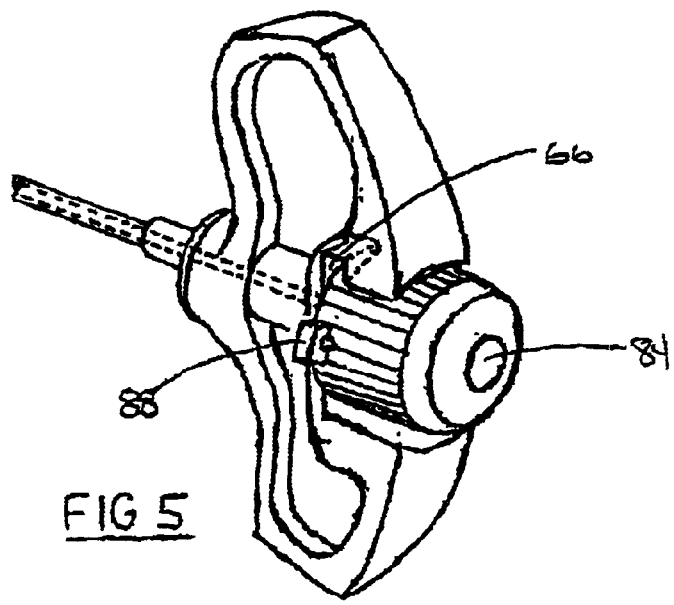
FIG. 5 illustrates a partial perspective view of the needle of FIG. 1 with the insert received within the sheath and the locking arms removed from the sleeves.

Referring now to FIGS. 4 and 5, inlet 44 is fixed to a handle 52 for grasping by the operator. Inlet 44 can be fixed to handle 52 by friction fit or other means as will occur to those of skill in the art. Preferably handle 52 is a molded polymer but other materials and forming processes can be used.

Handle 52 can be any shape suitable for grasping by an operator. According to a present embodiment, handle 52 has two wings 56 for grasping. A connector 60 is formed within handle 52. Connector 60 can be a female luer connector. Luer connectors are well know to those of skill in the art. Connector 60 has an externally threaded centre post 64 and internal sleeves 66. Centre post 64 has a hollow interior 68 that is aligned with, and extends from interior 38 thus presenting a continuous cylindrical hollow from handle 52 to outlet 40.

Referring to FIGS. 1–4, insert 28 is generally cylindrical with a tip 72 and opposing end 76. Tip 72 is bevelled at substantially the same angle as outlet 40 of sheath 24 creating bevelled face 80. Thus, when insert 28 is received within sheath 24, insert 28 can be oriented such that tip 72 is flush with outlet 40. Planar face 48 is aligned with bevelled face 80. The bevel angle is substantially identical between insert 28 and sheath 24, thus there is no step from tip 72 to outlet 40.

Referring now to FIGS. 4 and 5, opposing end 76 of insert 28 is fixed to a complementary connector 84. Complementary connector 84 can be any connector that is releasably attachable with connector 60 of handle 52. In the present embodiment, complementary connector 84 is a male luer connector. Complementary connector 84 is internally threaded to receive externally threaded centre post 64 when insert 28 is received within sheath 24. Complementary connector 84 has external locking arms 88 that are receivable by sleeves 66 when locking insert 28 within sheath 24. In the present embodiment, connector 60 and complementary connector 84 are a luer lock, however, it will be understood by those of skill in the art that connector 60 and complementary connector 84 can be any releasable attachment suitable for connecting sheath 24 and insert 28.

Figure 6:
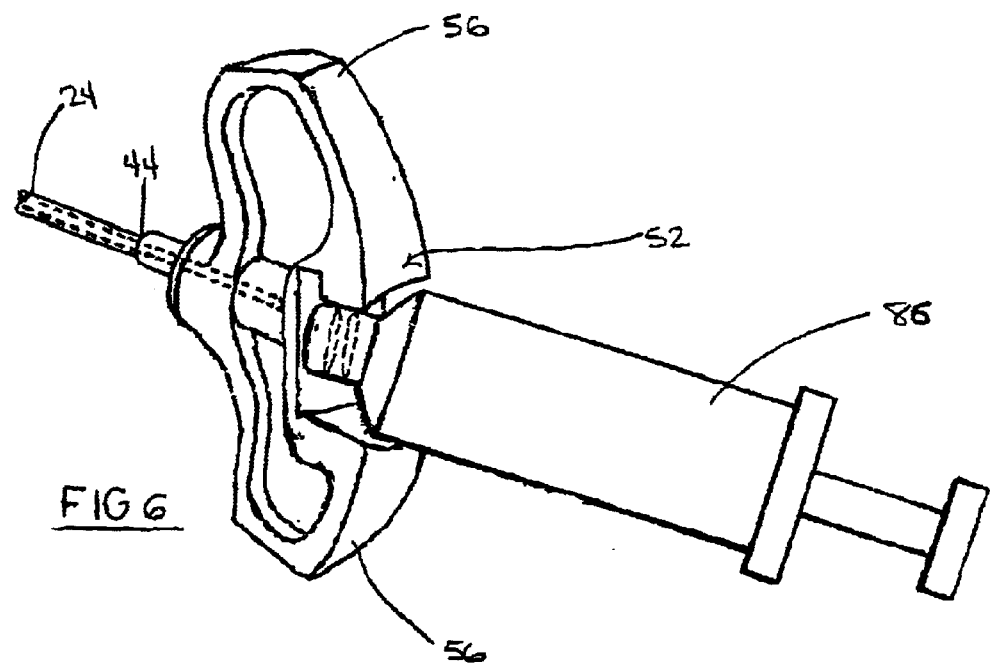
FIG. 6 illustrates a partial perspective view of the needle in FIG. 1 with the insert removed and a syringe attached.
Figure 7:
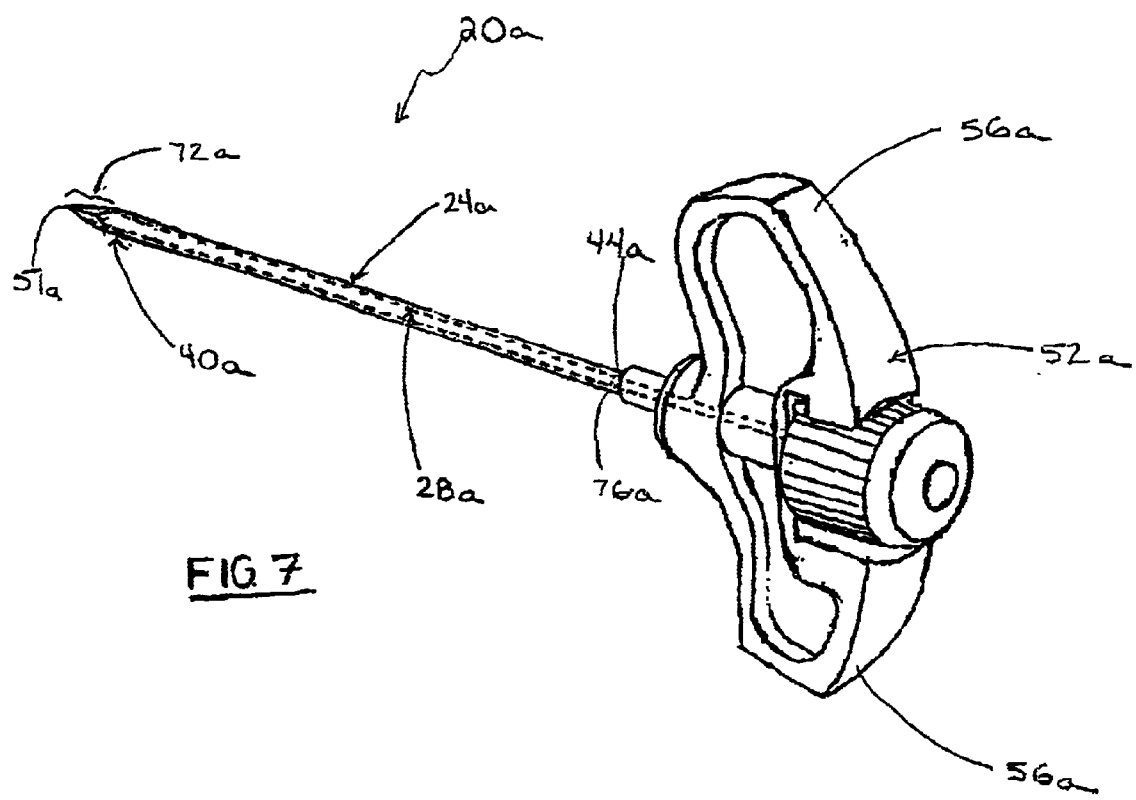
FIG. 7 illustrates a perspective view of a second embodiment of the cement delivery needle.

Referring now to FIG. 6, an injector can also be releasably attachable with connector 60 of inlet 44. The injector can be any part suitable for cement delivery through sheath 24 and into vertebral body 32. In the current illustration, the injector can be a syringe 86 such as the Medallion Syringe from Merit Medical Systems Inc., South Jordan Utah, 84095 U.S.A. Other suitable injectors can be used such as the Dyna Torque Injector from Parallax Medical, Inc., 455 Ravendale Dr., Suite B, Mountain View Calif., 94043, as will occur to those of skill in the art. Syringe 86 can contain cement for injection into inlet 44, through sheath 24 and into vertebral body 32.

Cement delivery needle 20 can be 10, 11, 13, or 14 gauge. Generally, 10 or 11 gauge needles are used for delivery of cement to a vertebral body in a lumbar or sacral vertebra and 13 or 14 gauge needles are used for delivery of cement to a vertebral body in a thoracic or cervical vertebra. Preferably, cement delivery needle 20 is from about eight cm to about twenty cm in length. More preferably, cement delivery needle 20 is from about ten cm to about fifteen cm in length. It will be understood by those skilled in the art, however, that the size and proportions of cement delivery needle 20 may vary depending on the vertebral body being filled and the subject.

Figure 11:
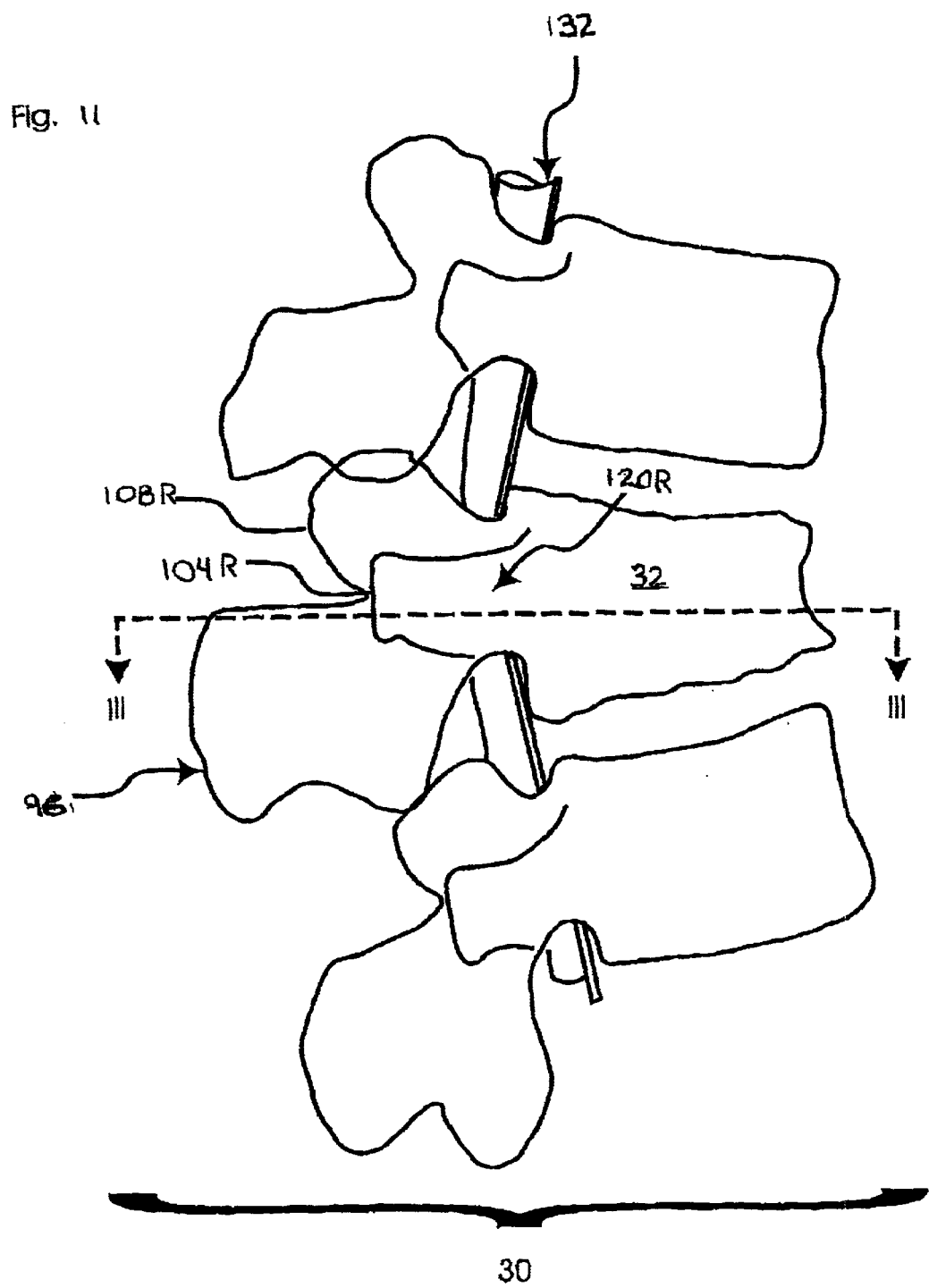
FIG. 11 illustrates a lateral view of 3 vertebrae wherein the middle vertebra has a condition suitable for treatment by vertebroplasty.
Figure 12:
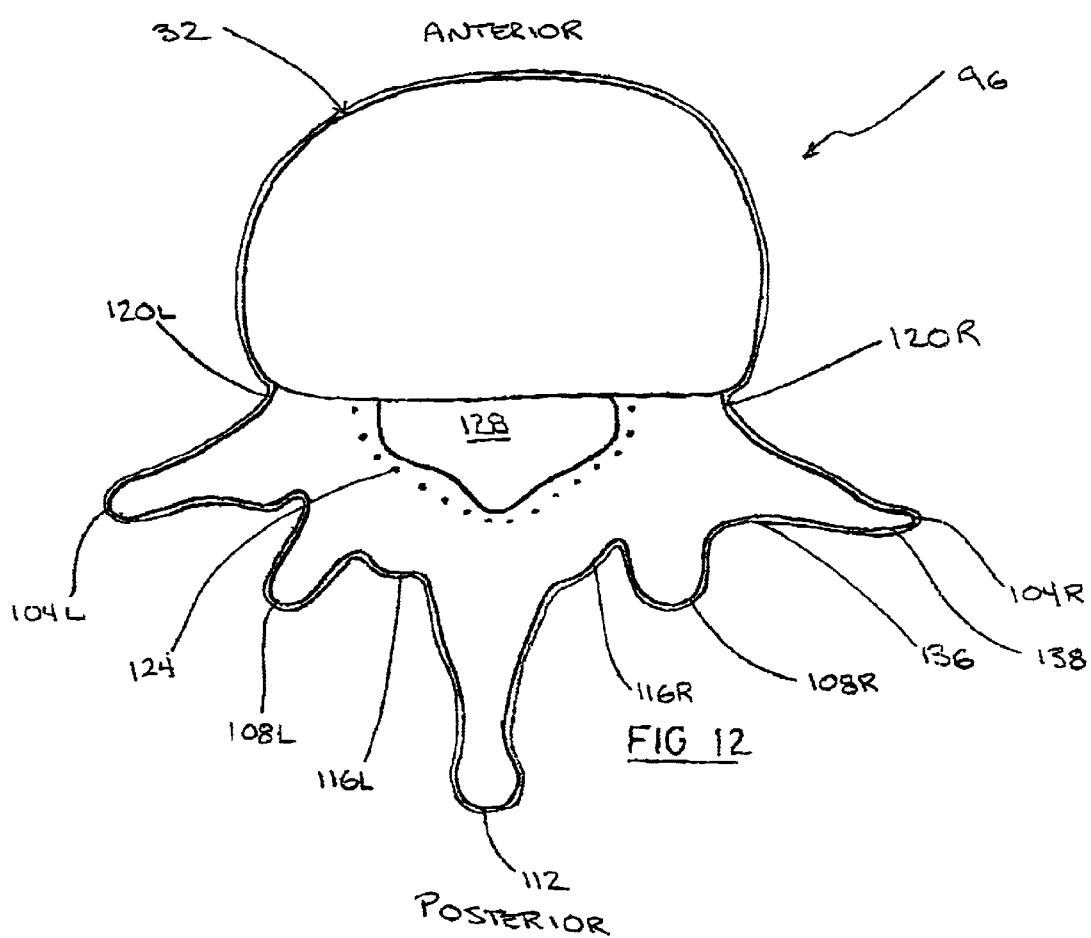
FIG. 12 illustrates an axial view of the compressed vertebra through line III—III of FIG. 9.

The use of needle 20 will now be described in accordance with an embodiment of the invention with reference to the foregoing and the attached Figures. Needle 20 is used when performing vertebroplasty on a patient having a vertebra 96. Referring to FIGS. 11 and 12, vertebra 96 has a right and left transverse process 104R, 104L, a right and left superior articular process 108R, 108L, and a spinous process 112 at the posterior of vertebra 96. Right and left lamina 116R, 116L lie intermediate spinous process 1 12 and superior articular processes 108R, 108L, respectively. Right and left pedicles 120R, 120L and lamina 116R, 116L cooperate to form the vertebral arch 124. The vertebral body 32 is located at the anterior of vertebra 96, and is joined to arch 124 at pedicles 120R, 120L. Arch 124 and vertebral body 32 define the spinal canal 128 through which spinal cord 132 passes. Periosteum 136, a layer of tissue, covers a cortex 138. Cortex 138 is the outer surface of vertebra 96.

The patient is placed in the prone position so that vertebra 96 is within the field of an imaging device, which in a present embodiment is an X-ray projection fluoroscopy imaging device. Other imaging devices can be used, as will occur to those of skill in the art. When the imaging device is 'on', vertebra 96 is projected onto a display. The skin overlying vertebra 96 is prepped and draped in the usual manner with sterile technique, as will be understood by those of skill in the art. An anaesthetic is injected into the skin, underlying fat and into periosteum 136 of the pedicle to be entered. For purposes of explaining the use of the present invention, it will be assumed that a right pedicle 120R will be entered first. Next, a skin incision of about five millimetres is made using a scalpel.

At this point, vertebroplasty needle 20 picked up by the operator. Typically, needle 20 is grasped by the operator such that the palm of the operator's hand abuts complementary connector 84 and the operator's fingers are folded around wings 56 of handle 52. Thus sheath 24 with insert 28 received therein, protrudes between the fingers of the operator.

Figure 13:
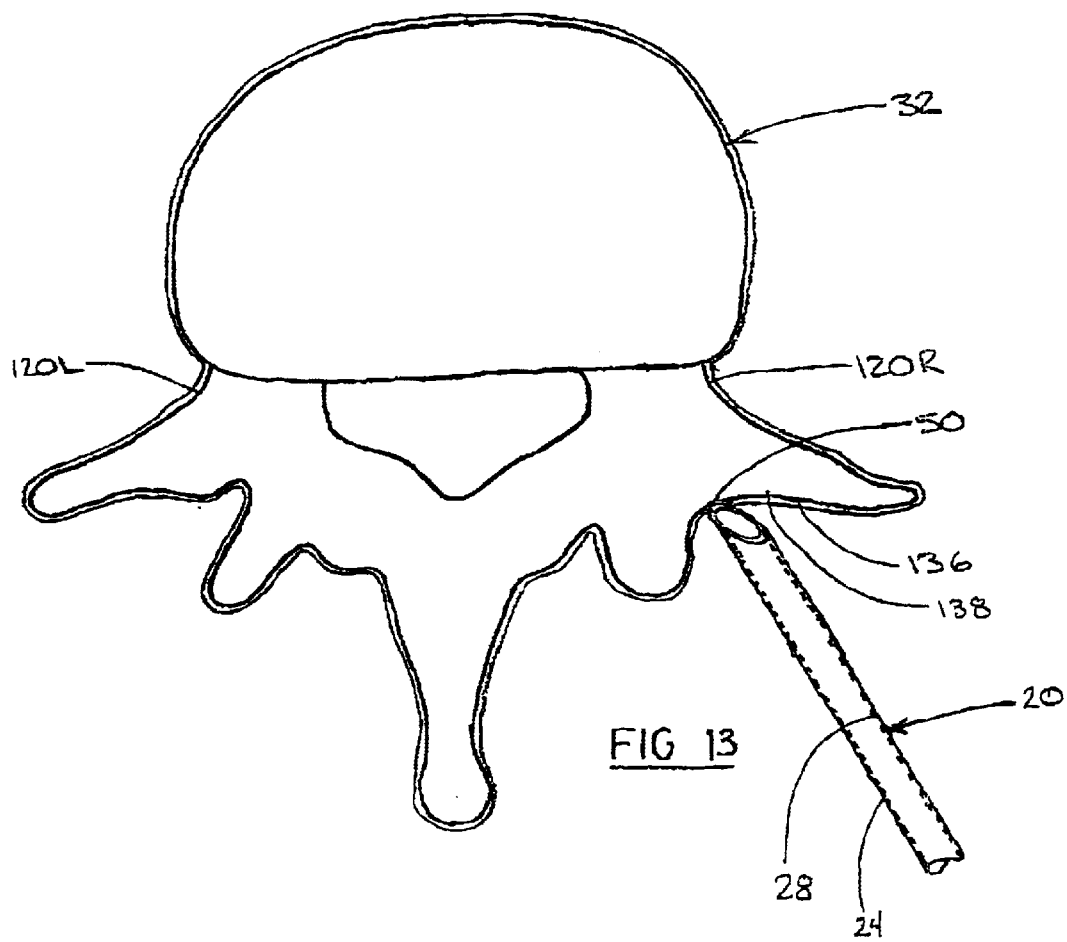
FIG. 13 illustrates an axial view of the vertebra in FIG. 10 showing the insertion of the cement delivery needle in FIG. 1 to the junction of the periosteum and the left pedicle.
Figure 14:
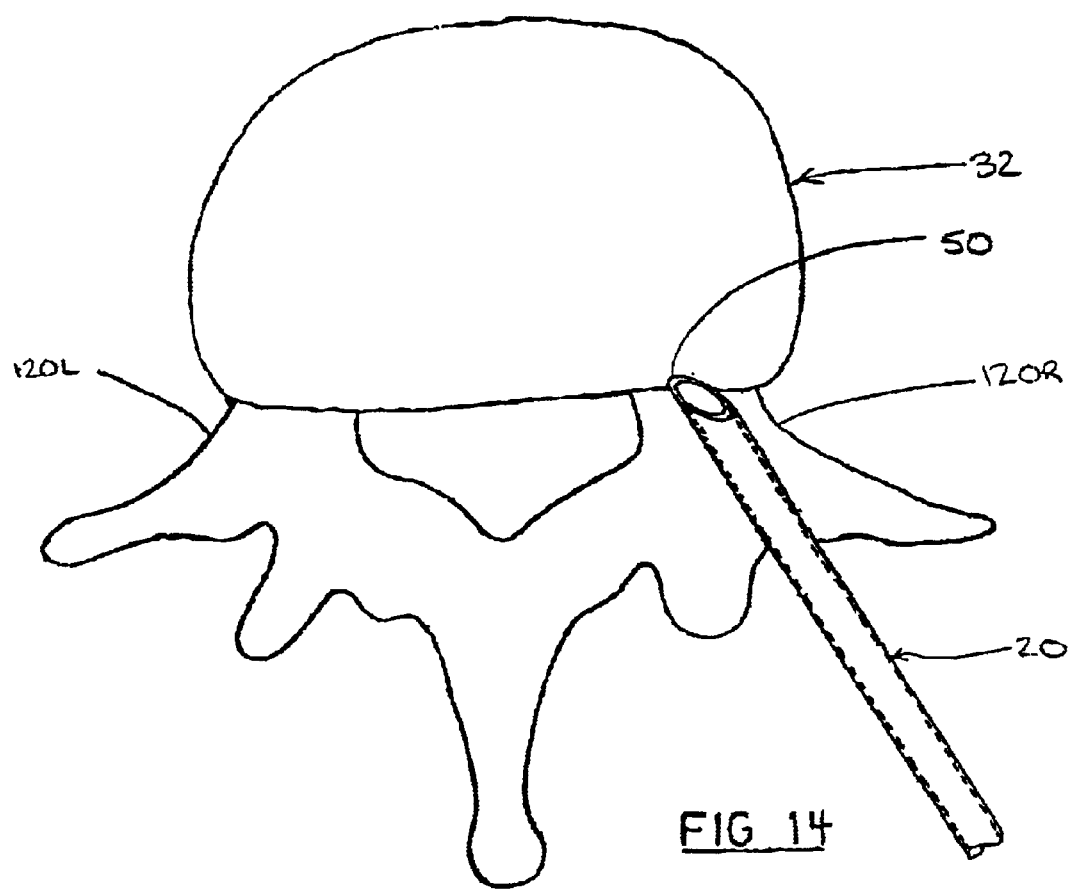
FIG. 14 illustrates an axial view of the vertebra in FIG. 10 showing the insertion of the cement delivery needle in FIG. 1 to the transition from the right pedicle to the vertebral body.
Figure 15:
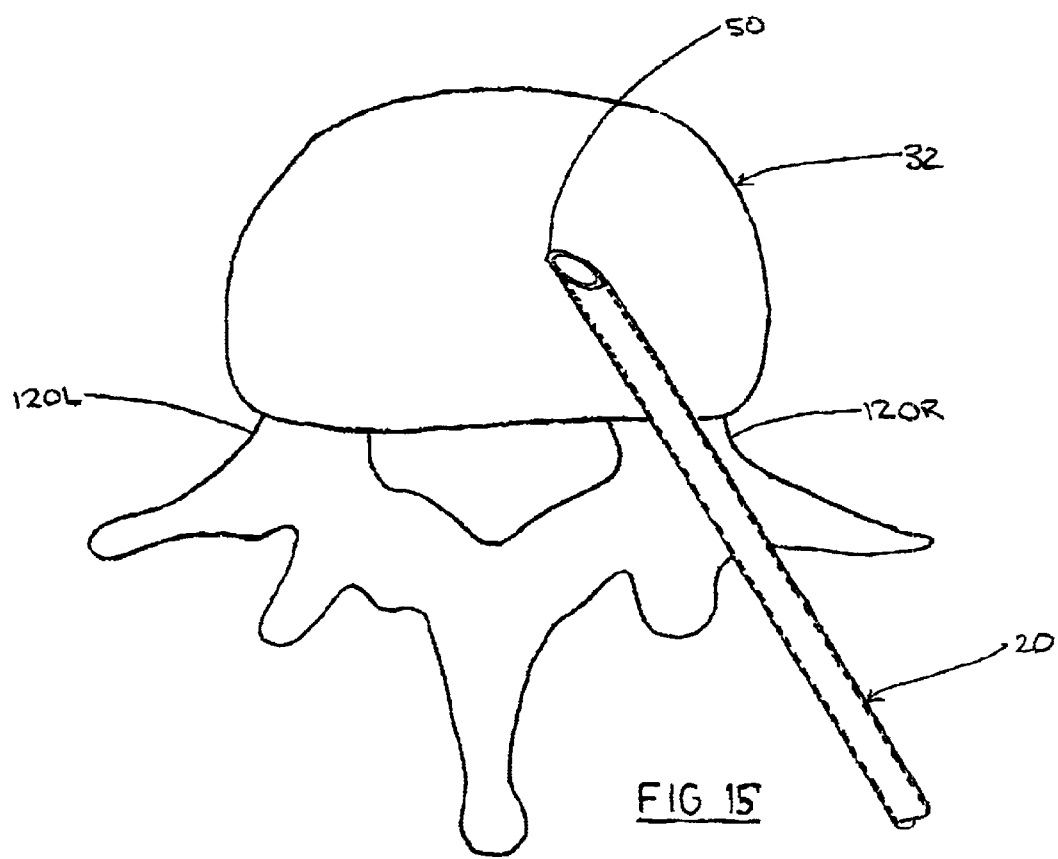
FIG. 15 illustrates an axial view of the vertebra in FIG. 10 showing the cement delivery needle in FIG. 1 inserted into the vertebral body.

Referring to FIGS. 12–16, needle 20 is inserted into the incision and passed down right pedicle 120R, preferably until it enters vertebral body 32 and reaches the junction of the anterior and middle thirds. Needle 20 is inserted until leading edge 50 meets periosteum 136, as shown in FIG. 13. Additional applied force is then required to pass through periosteum 136 and cortex 138 and into right pedicle 120R. Needle 20 with leading edge 50 is inserted further to the transition from right pedicle 120R to vertebral body 32, as shown in FIG. 14. Again, additional applied force is required to pass through the transition and into vertebral body 32. Needle 20 is further inserted until leading edge 50 reaches the junction of the anterior and middle thirds of vertebral body 32, as shown in FIG. 15.

At this point complementary connector 84 is released from connector 60 and insert 8 is slideably removed from sheath 24. The position of sheath 24 is maintained such that leading edge 50 is still in vertebral body 32 after insert 28 is removed from sheath 24.

Figure 16:
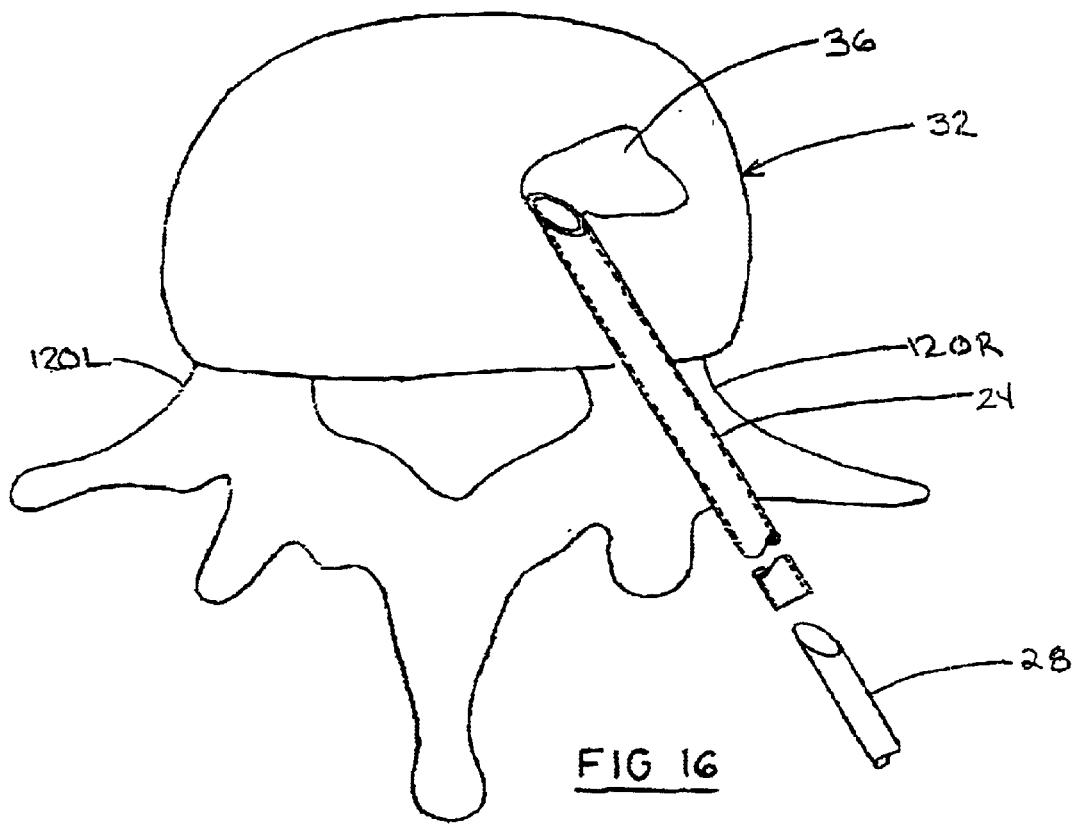
FIG. 16 illustrates an axial view of the vertebra in FIG. 10 showing the cement delivery needle in FIG. 1 inserted into the vertebral body wherein the insert is removed from the sheath and a cement is delivered to the vertebral body.

A suitable cement 36 for strengthening a vertebral body is then prepared. Cement 6, can be detected by an imaging device. Prepared cement 36 is inserted into the syringe and the syringe is releasably connected to connector 60 of sheath 24. Referring now to FIG. 16, cement 36 is injected through sheath 24 and into vertebral body 32. The direction of cement 36 injected into vertebral body 32 can be controlled as cement 36 is ejected from bevelled outlet 40. Thus, sheath 24 can be turned to aim the bevelled outlet 40 and thereby direct the flow of cement 36 in vertebral body 32. As filling of vertebral body 32 progresses, sheath 24 can be rotated about axis 46 to direct cement 36 in a preferred direction or to direct cement 36 away from a disc space of the vertebra, as desired.

At this point, a decision can be made as to whether a sufficient quantity of cement 36 has been injected. This decision is made using known criteria and is typically made by the radiologist, physician or other vertebroplasty professional who is performing the method. If it is determined that enough cement 36 has been injected to provide the desired strength to vertebral body 32, then the treatment method is complete and the patient is prepared for removal from the X-ray room and transferred to the observation area. If it is determined that not enough cement 36 has been injected into the vertebral body 32, then a second injection can be performed by inserting needle 20 through the other pedicle, in this case left pedicle 120L.

In another embodiment of the present invention all features are given the same label designation as in the first embodiment and are suffixed with the letter a. Referring to FIGS. 7–10, sheath 24a is generally a hollow cylinder with an interior 38a, an outlet 40a and an inlet 44a. The cross-sectional area of interior 38a is not reduced at outlet 40a. The diameter of interior 38a, is substantially constant from inlet 44a to outlet 40a. Sheath 24a is cylindrically centred about axis 46a and has three substantially equal, inwardly bevelled surfaces 48a defining outlet 40a. Each surface 48a is bevelled toward axis 46a. Thus, sheath 24a has 3 sharp points 49a at outlet 40a. Each sharp point 49a is present at each intersection of two bevelled surfaces 48a. Each bevelled surface 48a is at substantially the same angle to axis 46a. Preferably, each bevelled surface 48a is at an angle of from about fifteen degrees to about seventy-five degrees. More preferably, each bevelled surface 48a is at an angle of from about thirty degrees to about sixty degrees. It is presently preferred however, that each bevelled surface 48a is at an angle of about forty-five degrees to axis 46a. As in the first embodiment, inlet 44a is fixed to a handle 52a for grasping by the operator. Handle 52a in the present embodiment can be the same as handle 52 in the first embodiment.

Insert 28a is generally cylindrical with a tip 72a and opposing end 76a. Tip 72a has three substantially equal, inwardly bevelled faces 80a. Each face 80a is bevelled at substantially the same angle as bevelled surfaces 48a. Thus, all three bevelled faces 80a intersect at a leading point 51a that protrudes from sheath 24a. When insert 28a is received within sheath 24a, insert 28a can be oriented such that each of bevelled faces 80a is aligned with one of bevelled surfaces 48a. The bevel angle is substantially identical between insert 28a and sheath 24a, thus there is no step from tip 72a to sheath 24a, to present three continuous bevelled faces from sheath 24a to tip 72a. Opposing end 76a of insert 28a in the present embodiment can be the same as opposing end 76 of insert 28 in the first embodiment. Other features of the present embodiment of needle 20a not outlined herein can be the same as those features of the first embodiment of needle 20.

The use of needle 20a, in the present embodiment is similar to the use of needle 20 in the first embodiment. After preparation of the patient, needle 20a can be grasped by the operator the same way as needle 20 is grasped, as outlined above. Referring to FIGS. 13–15 and 17, needle 20a is inserted into the incision and passed down the right pedicle 120R, preferably until it enters vertebral body 32 and enters the junction of the anterior and middle thirds. Needle 20a is inserted until leading point 51a meets periosteum 136. Additional applied force is then required to pass through periosteum 136 and into right pedicle 120R. Leading point 51a of needle 20a is inserted further to the transition from right pedicle 120R to vertebral body 32. Again, additional applied force is required to pass through the transition and into vertebral body 32. Needle 20a is further inserted until leading point 51a reaches the unction of the anterior and middle thirds of vertebral body 32.

Figure 17:
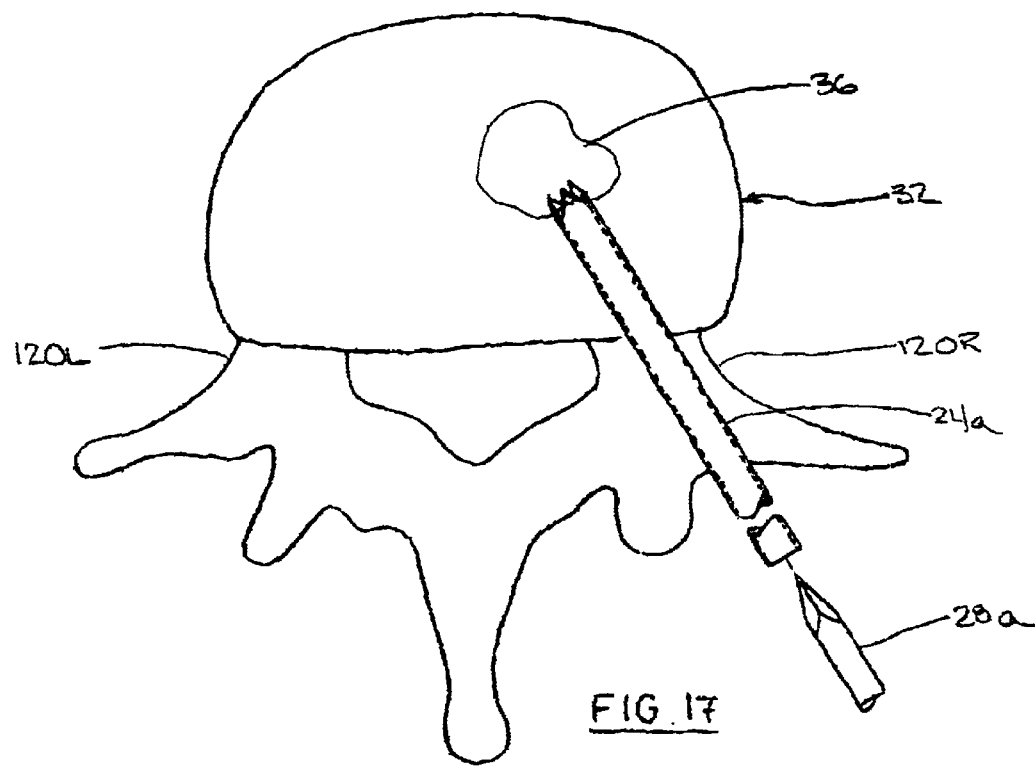
FIG. 17 illustrates an axial view of the vertebra in FIG. 10 showing the cement delivery needle in FIG. 7 inserted into the vertebral body wherein the insert is removed from the sheath and the cement is delivered to the vertebral body.

Insert 28a is then slideably removed from sheath 24a and cement 36 is injected through sheath 24a as in the first embodiment. Referring now to FIG. 17, the flow of cement 36 is expelled from an outlet with three inwardly bevelled surfaces 48a, as described above.

As will now be apparent to those of skill in the art, needles 20 and 20a can also be used to take a bone or tissue biopsy sample. After needle 20, 20a is inserted into the patient, insert 28, 28a can be slideably removed from sheath 24, 24a. Sheath 24, 24a can then be pushed into the target bone or tissue, effectively coring a biopsy sample therewithin.

While the embodiments discussed herein are directed to particular implementations of the present invention, it will be apparent that the subsets and variations to these embodiments are within the scope of the invention. For example, the size and shape of the handle can differ. The releasably attachable connector and complementary connector can be any releasable attachment. The end of the needle with the outlet and tip can have two bevelled faces thus presenting a substantially continuous leading edge across both the sheath and insert. Each bevelled face being substantially continuous and having no step between the sheath and the insert. Alternatively, the end of the needle with the outlet and tip can have more than three bevelled faces. Again, each bevelled face being substantially continuous and having no step between the sheath and the insert. The end of the needle with the outlet and tip can also be conical, thus presenting a leading point on the insert. Similarly, the sheath and insert are substantially continuously conical and there is no substantial step between the insert and the sheath. The shape of any of the features can differ while still performing the same function. Furthermore, a surface or cone can be considered to be a plurality of edges. Thus, a substantially continuous surface or cone with no step between the insert and sheath can be considered to be a plurality of substantially continuous edges.

The present invention provides a novel cement delivery needle for expressing bone cement or a suitable biomaterial into a vertebral body. In one embodiment there is provided a cement delivery needle with a sheath and an insert receivably removable within the sheath. The sheath has an interior, an outlet, and an inlet. The insert has a tip and an opposing end. The tip of the insert and the outlet of the sheath are tapered and alignable such that they present a continuous edge when the insert is received within the sheath. Because there is no step between the sheath and the insert the cement delivery needle can be easier to insert into the patient. Insertion of the needle can require less applied force and the use of a hammer can be avoided when the needle passes through the periosteum into the pedicle and in the transition from the pedicle into the vertebral body. Further, less required force can allow the operator greater control during insertion of the needle. Also, the cement can be delivered to the vertebral body more easily as the cross sectional area of the interior of the sheath is not reduced at the outlet of the sheath. The cement also disperses easily from the bevelled edges, thus more cement can be delivered to the vertebral body.

While the present invention has been described with reference to preferred and specifically illustrated embodiments, it will of course be understood by those skilled in the arts that various modifications to these preferred and illustrated embodiments may be made without departing from the spirit and scope of the invention.

All publications, patents and patent applications referred to herein are incorporated by reference in their entirety to the same extent as if each individual publication, patent or patent application was specifically and individually indicated to be incorporated by reference in its entirety.

What is claimed is:

1. A method for passing a needle into a vertebral body, said needle having a sheath and an insert, said sheath having an inlet, a tapered outlet and a connector fixed to said inlet, an interior of said sheath having a cross-sectional area that is substantially constant from said inlet to said outlet, said insert being generally cylindrical and receivably removable within said sheath, said insert having a tip, an opposing end and a complementary connector fixed to said opposing end, said method comprising the steps of:

inserting said tip into said sheath;

aligning said tip with said tapered outlet to present a continuous edge;

attaching said complementary connector with said connector to lock said tip within said sheath;

piercing the skin lying above a periosteum of a vertebrae along a transpedicular approach;

applying a first force to said needle to pierce said periosteum with said edge and create an opening of sufficient size for said needle to pass therethrough;

passing said needle through a pedicle;

applying a second force to said needle to pierce a junction of said pedicle and said vertebral body with said edge, thereby creating an opening of sufficient size to allow said needle to pass therethrough.

2. The method defined in claim 1, wherein said needle is passed through said pedicle corresponding to a transpedicular approach.

3. The method defined in claim 1, wherein said needle is passed through said pedicle corresponding to a lateral approach.

4. The method defined in claim 1, comprising the further step of removing said insert from said sheath.

5. The method defined in claim 4, comprising the further step of injecting a bone cement through said sheath and into said vertebral body.

6. The method defined in claim 4, comprising the further step of obtaining a biopsy sample of said vertebral body.

* * * * *